(12) United States Patent
Michaels et al.

(10) Patent No.: US 8,651,531 B2
(45) Date of Patent: Feb. 18, 2014

(54) METHOD AND APPARATUS FOR THE DISPOSAL OF WASTE FLUIDS

(75) Inventors: Thomas L. Michaels, McHenry, IL (US); Kenneth Horton, Jr., Kildeer, IL (US); Shannon C. Ingram, San Antonio, TX (US)

(73) Assignee: Allegiance Corporation, McGaw Park, IL (US)

( * ) Notice: Subject to any disclaimer, the term of this patent is extended or adjusted under 35 U.S.C. 154(b) by 664 days.

(21) Appl. No.: 12/337,220

(22) Filed: Dec. 17, 2008

(65) Prior Publication Data

US 2009/0151793 A1   Jun. 18, 2009

Related U.S. Application Data

(62) Division of application No. 10/782,471, filed on Feb. 19, 2004, now Pat. No. 7,481,243.

(51) Int. Cl.
*F16L 39/00* (2006.01)

(52) U.S. Cl.
USPC ..... 285/201; 285/202; 285/123.3; 285/124.2; 285/137.11; 285/924

(58) Field of Classification Search
USPC .............. 285/136.1, 137.11, 141.1, 201–202, 285/213, 123.3, 123.15, 124.1, 124.2, 285/13–14, 924; 215/11.5, 386, DIG. 8; 206/219–220
See application file for complete search history.

(56) References Cited

U.S. PATENT DOCUMENTS

| | | |
|---|---|---|
| 905,818 A | 12/1908 | Langford |
| 954,270 A | 4/1910 | Eberman |
| 997,584 A | 7/1911 | Rosenberg |
| 1,068,102 A | 7/1913 | Brown |
| 1,118,971 A | 12/1914 | Tomko |
| 1,212,004 A | 1/1917 | Berg |
| 1,269,910 A | 6/1918 | Cope |
| 1,609,065 A | 11/1926 | Corwin |
| 1,643,025 A | 9/1927 | Meggenhofen |
| 1,954,105 A | 4/1934 | Stoddard |
| 2,223,012 A * | 11/1940 | Wanderski et al. ........ 222/400.7 |
| 2,512,479 A | 6/1950 | Callejo |
| 2,690,717 A | 10/1954 | Goodrie |
| 2,699,731 A | 1/1955 | Pollock et al. |
| 2,741,258 A | 4/1956 | Bletcher et al. |

(Continued)

FOREIGN PATENT DOCUMENTS

WO   WO 00/12403   3/2000

OTHER PUBLICATIONS

BEMIS Manufacturing Company, VAC-U-PORT Confined Liquid Infectious Waste Management System, product literature, 1998.

(Continued)

*Primary Examiner* — Aaron Dunwoody
*Assistant Examiner* — Fannie Kee
(74) *Attorney, Agent, or Firm* — Arent Fox LLP

(57) ABSTRACT

An apparatus for disposing of waste fluids includes a conduit system adapted to transport waste fluid from a receptacle to a sanitary sewer using an eductor having a venturi device. The conduit system includes first and second conduits. First and second connectors are used to connect the first conduit to the second conduit. The second connector includes a flap that acts as a check valve.

6 Claims, 13 Drawing Sheets

(56) References Cited

U.S. PATENT DOCUMENTS

| | | | |
|---|---|---|---|
| 2,899,971 A | | 8/1959 | Munter |
| 3,183,923 A | | 5/1965 | Henrikson |
| 3,646,935 A | | 3/1972 | Holbrook et al. |
| 4,014,052 A | | 3/1977 | Wolos |
| 4,114,782 A | * | 9/1978 | Berry .................... 222/382 |
| 4,285,445 A | | 8/1981 | Molen et al. |
| 4,344,469 A | | 8/1982 | Brown |
| 4,386,637 A | | 6/1983 | Buchanan et al. |
| 4,422,829 A | | 12/1983 | Buchanan |
| 4,696,322 A | | 9/1987 | Knapp et al. |
| 4,697,610 A | | 10/1987 | Bricker et al. |
| 4,832,237 A | * | 5/1989 | Hurford, Jr. ............ 222/464.1 |
| 5,083,587 A | | 1/1992 | Tarjan |
| 5,176,165 A | | 1/1993 | Traylor |
| 5,217,038 A | | 6/1993 | Pinder |
| 5,380,308 A | | 1/1995 | Gunya et al. |
| 5,725,516 A | | 3/1998 | Cook et al. |
| 5,741,237 A | | 4/1998 | Walker |
| 5,776,118 A | | 7/1998 | Seifert et al. |
| 5,776,260 A | | 7/1998 | Dunn et al. |
| 5,792,126 A | | 8/1998 | Tribastone et al. |
| 5,960,837 A | | 10/1999 | Cude |
| 6,142,345 A | * | 11/2000 | Laible .................... 222/189.1 |
| 6,494,869 B1 | * | 12/2002 | Hand et al. ................ 604/319 |
| 6,543,654 B1 | | 4/2003 | Uhl et al. |
| 6,626,877 B2 | | 9/2003 | Anderson et al. |
| 2007/0129694 A1 | | 6/2007 | Opie et al. |

OTHER PUBLICATIONS

DEROYAL, Aqua-box Canister and Liner Evacuation System, Dec. 5, 2003, 2 pages.
Fox Valve, Fox Liquid Educa/tors, Bulletin 101.
Fox Valve Development Corp, Fox Venturi Products, Bulletin 203.

* cited by examiner

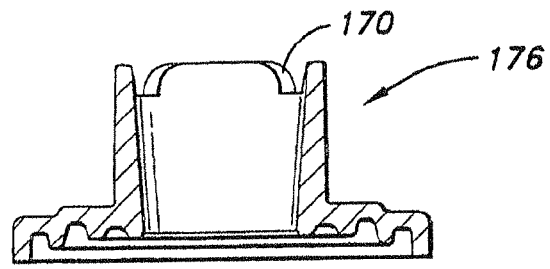
FIG. 13
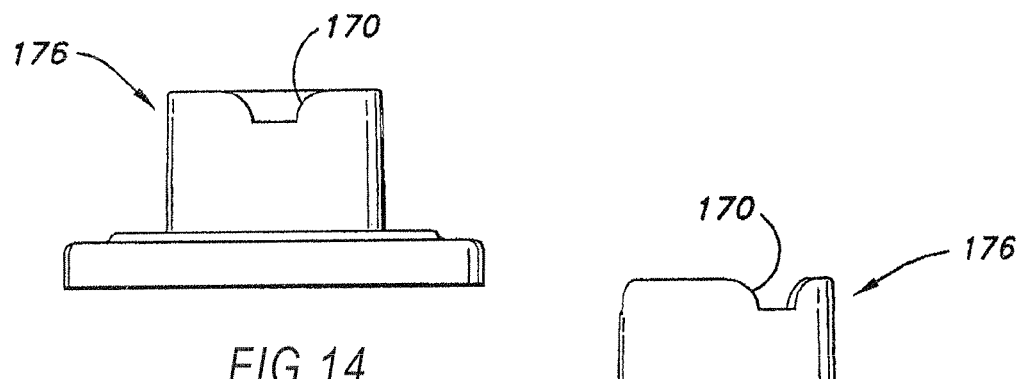
FIG. 14
FIG. 15
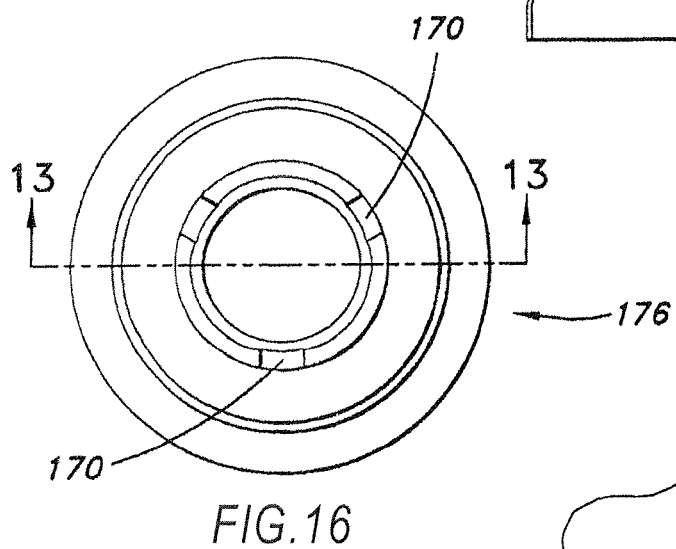
FIG. 16
FIG. 17

METHOD AND APPARATUS FOR THE DISPOSAL OF WASTE FLUIDS

This is a Divisional Application, which claims the benefit of pending U.S. patent application Ser. No. 10/782,471, filed Feb. 19, 2004. The disclosure of the prior application is hereby incorporated herein in its entirety by reference.

BACKGROUND OF THE INVENTION

1. Field of the Invention

This invention relates to apparatuses and methods for disposing of waste fluids. More particularly, this invention relates to apparatuses and methods for disposing of waste fluids generated during medical procedures to a sanitary sewer.

2. Description of the Related Art

It is well known that blood, other body fluids and irrigating solutions must be removed from the body of patients when they undergo medical procedures, such as surgery. Medical providers, such as doctor's offices and hospitals, use a variety of different containers and apparatuses for collecting such fluids. These fluids must then be disposed of in an appropriate manner.

Different methods of disposing of such fluids are known. One method is to dispose of the fluids and the container they are held in together as a unit. While this method works well for its intended purpose, medical waste removers typically charge by the weight of material being disposed. Thus, including the collected fluids along with the container increases the cost of such removal.

Another method is to solidify the fluids rendering them either non-infectious or viscous. This method also works well for its intended purpose but also is relatively expensive because the solidified fluids are still a significant portion (weight) of the waste to be disposed. As noted above, medical waste removers typically charge by the weight of material being disposed.

Another method, assuming the waste fluids are of the type that can be placed within the sanitary sewer, is to simply pour the fluids out of the container and down the sanitary drain. This method has the advantage of minimizing the disposal costs because, without the fluids, the overall weight of items that must be removed by medical waste removers is reduced. As such, this method works well for its intended purpose when done carefully. However, heightened awareness concerning employee safety makes this method less attractive. Pouring of such waste fluids may disperse aerosols and may result in residual spilling and splattering of the waste fluids.

It is known to reduce these disadvantages with the use of a venturi device. Venturi devices are well known to be effective in removing fluids from a container. Examples are provided in U.S. Pat. Nos. 954,270, 997,584, 1,068,102, and 1,118,971. Pinder, in U.S. Pat. No. 5,217,038, utilizes pressurized water and a venturi device to remove surgical waste fluids from a container and transport the fluids into a sanitary drain. Bemis Manufacturing Company, Health Care Products Group, of Sheboygan Falls, Wis., provides a similar assembly.

However, neither the Pinder nor Bemis assemblies have the advantages provided by the inventors of this patent. These advantages are described below.

SUMMARY OF THE INVENTION

According to one aspect of the present invention, an apparatus for transporting waste fluid from a first receptacle to a disposal site is provided. A first conduit has first and second ends and a second conduit has first and second ends. A first connector is attached to the second end of the first conduit and a second connector is attached to the first end of the second conduit. The second connector is selectively and operatively connectable to the first connector to establish flow through the conduits. A control means for controlling the flow of the flowable substance is also included.

According to another aspect of the invention, the invention is used in environments where the associated waste fluid is a fluid from a human body, such as is generated during surgery.

According to another aspect of the invention, the control means for controlling the flow of the associated waste fluid includes a flow direction device. The flow direction device includes a flap. The flap is selectively movable between an open and a closed position.

According to another aspect of the invention, the first connector which is attached to the second end of the first conduit includes an outer wall and an inner wall, both of which are generally cylindrical. An inner support member is disposed between the inner and outer walls and thereby joins them into an integral member. Holes located in the inner support member enable pressure on one side of the connector to be equalized with pressure on the other side of the connector.

According to another aspect of the invention, the mode of power to move the fluid from the receptacle to the sanitary sewer is supplied by an eductor device.

Still other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein:

FIGS. 13-17 are of a second connector according to the invention.

FIGS. 17A-20 are of a second connector according to the invention.

DETAILED DESCRIPTION OF THE PREFERRED EMBODIMENTS

Figure 1:
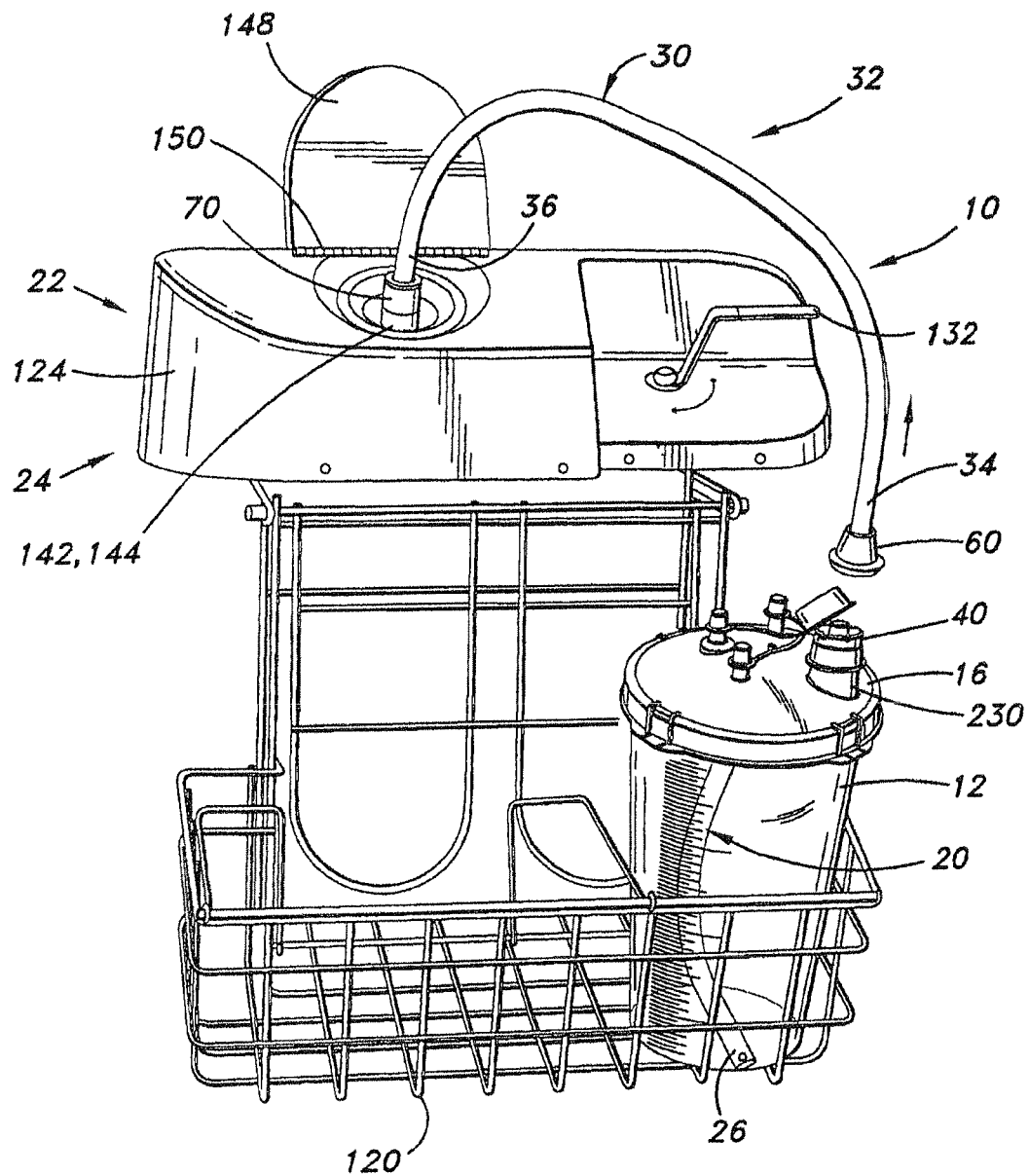
FIG. 1 is a perspective view of an apparatus according to the invention.

Referring now to the drawings wherein the showings are for purposes of illustrating a preferred embodiment of the invention only and not for purposes of limiting the same, FIG. 1 shows the inventive apparatus 10 that is used to remove waste fluid (not shown) from a canister or first receptacle 12. It should be noted that the inventive device will work with virtually any fluid, including fluids with certain solid matter mixed in. A cap 16 fits over the first receptacle 12 and operates as a lid. Preferably the cap 16 fits snuggly onto the top of the first receptacle 12 as is commonly known in the art. In the preferred embodiment, the first receptacle 12 sits in a wire basket 120. It is also preferred that the wire basket 120 is large enough to carry at least two first receptacles 12.

Figure 2:
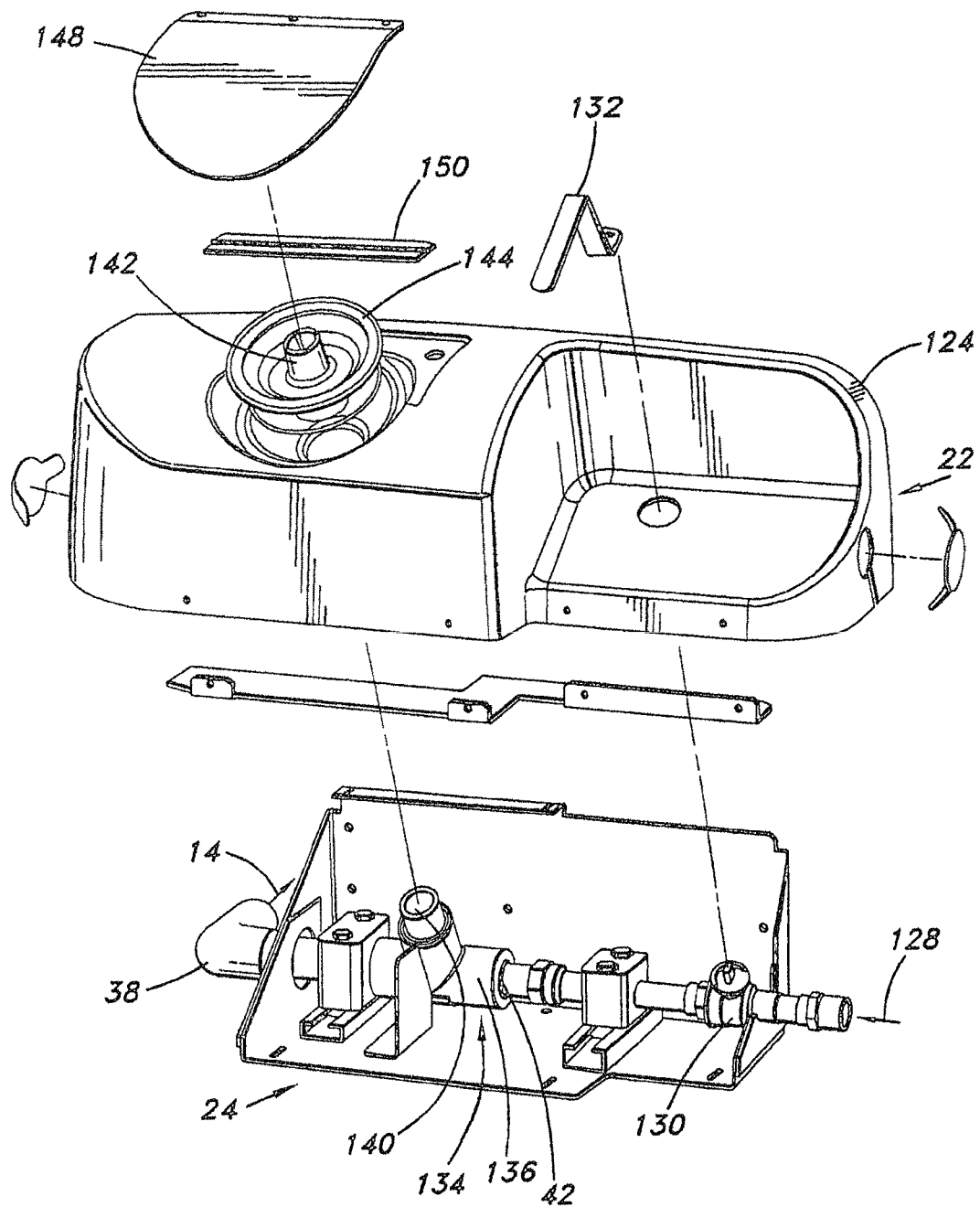
FIG. 2 is an assembly view of the eductor pump assembly of the apparatus shown in FIG. 1.
Figure 2A:
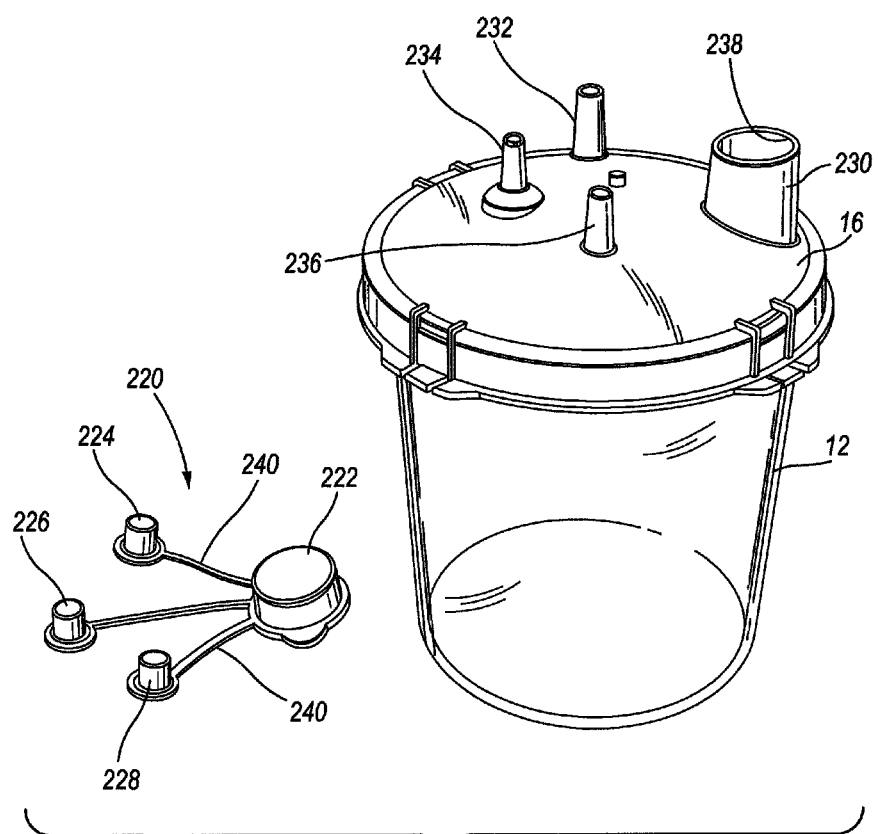
FIG. 2A is a perspective view of a first receptacle and cap with a cap attachment shown unattached.
Figure 2B:
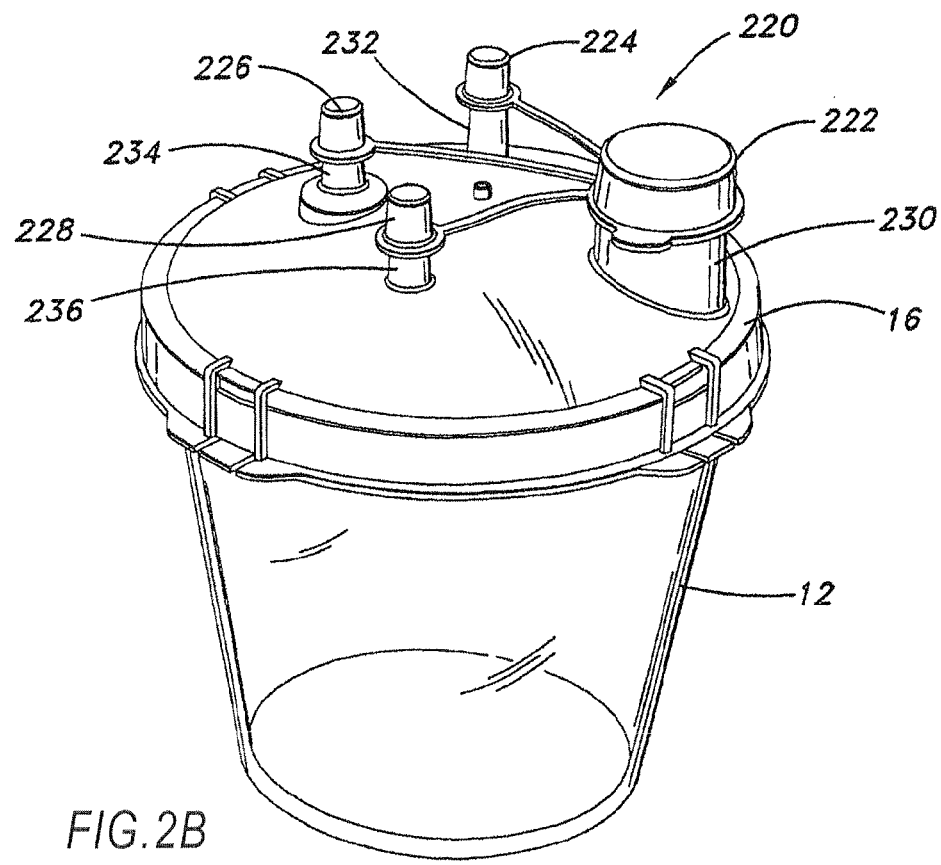
FIG. 2B is a perspective view of a first receptacle and cap similar to FIG. 2A except with the cap attachment shown attached to the cap.
Figure 2C:
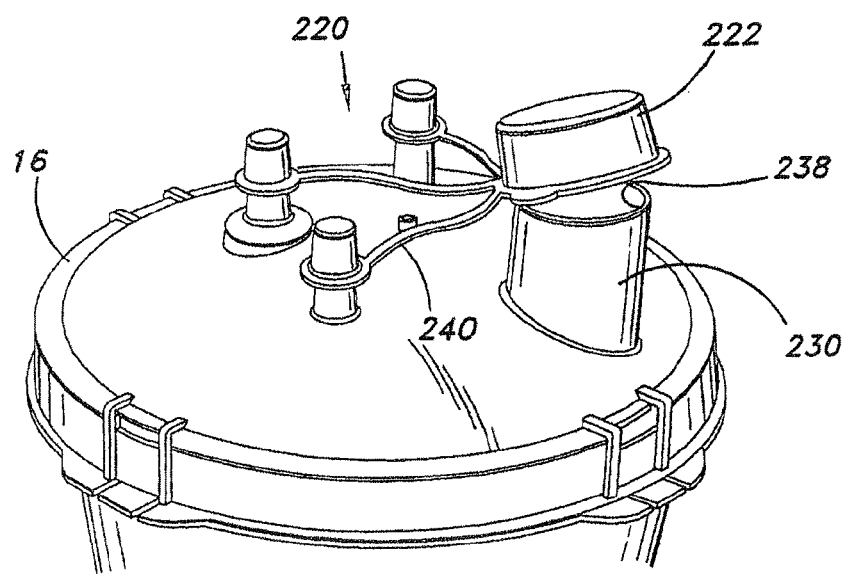
FIG. 2C is a perspective view of a first receptacle and cap similar to FIG. 2B except with the first lid shown unattached to the first tower.

With reference now to FIGS. 2A, 2B and 2C, a typical first receptacle 12 and cap 16 is shown. Also shown is an optional, but standard, cap attachment 220. The cap attachment 220 shown includes four lids 222, 224, 226, 228 each properly sized to cover and seal four corresponding towers 230, 232, 234, 236 that extend from the cap 16. FIG. 2B shows the lids 222, 224, 226, 228 attached to and covering the towers 230, 232, 234, 236. While the number and purposes for the towers can vary as required, it is noted that first tower 230 defines an opening 238 through the cap 16. Thus, when the cap 16 is properly attached to the first receptacle 12, the first tower 230 communicates with the contents of the first receptacle 12. The lids are preferably attached to each other, such as with webbing 240, so that only a portion of the lids need to be attached to the corresponding towers for the cap attachment 220 to be attached to the cap 16. FIG. 2C, for example, shows the cap attachment 220 attached to the cap 16 except that the first lid 222 is not attached to the first tower 230. This frees the first lid 222 to be available for another purpose that will be discussed below.

With reference now to FIGS. 1 and 2, the apparatus 10 includes a suction means 22 and a conduit means 32. The suction means 22 is used to draw fluid waste (not shown) from within the first receptacle 12 through the conduit means 32 and then to a disposal site (one embodiment shown with reference 14 in FIG. 2). The disposal site can be any appropriate destination for the fluid waste. In some applications, the disposal site may be a second receptacle (not shown). In such cases, the fluid is transferred from the first receptacle 12 into the second receptacle. In the preferred embodiment, as illustrated in FIG. 2, the disposal site is actually the plumbing system of the hospital, specifically the sanitary sewer 14.

With continuing reference to FIGS. 1 and 2, the suction means 22 can be of any type chosen with sound engineering judgment including a mechanically or electrically driven pump. In the preferred embodiment, the suction means 22 is an eductor pump assembly 24. Waste fluid enters the eductor pump assembly 24 at the pump inlet 142, which preferably includes a quick connect fitting 144, and exits the eductor pump assembly 24 to the sanitary sewer 14. With special reference to FIG. 2, the preferred eductor pump assembly 24 includes a decorative housing 124. A top 148, with hinge 150, can be used to cover and protect the pump inlet 142 when it is not being used. Within the housing 124 can be seen the eductor 134. The eductor 134, as is commonly known, operates with a venturi and a source of water, such as is available from the hospital water supply system. The operation of the eductor 134 will be discussed further below. A source of pressurized clean water, such as is readily available from city or well water sources, enters at water inlet 128. A valve 130, preferably a quarter turn valve, is operated via a handle 132. By a quarter turn valve it is meant that the valve can be operated from its full closed position to its full open position by moving the handle 132 through a range of 90 degrees. This invention will work equally well with valves having different handle operating ranges. The eductor 134 is next in line in the piping system followed by the outlet 38 to the sanitary sewer 14. The eductor 134 has a first inlet 42 that receives the water source and also a second inlet or ingress 140 that receives the waste fluid. When the valve 130 is opened, water flows through the water inlet 128, through the valve 130 and through the eductor 134. This water flow causes the eductor 134 to create a suction force on the second inlet 140 thereby drawing the waste fluid into the eductor 134. Both the water and the waste fluid are then disposed into the sanitary sewer 14.

Figure 23:
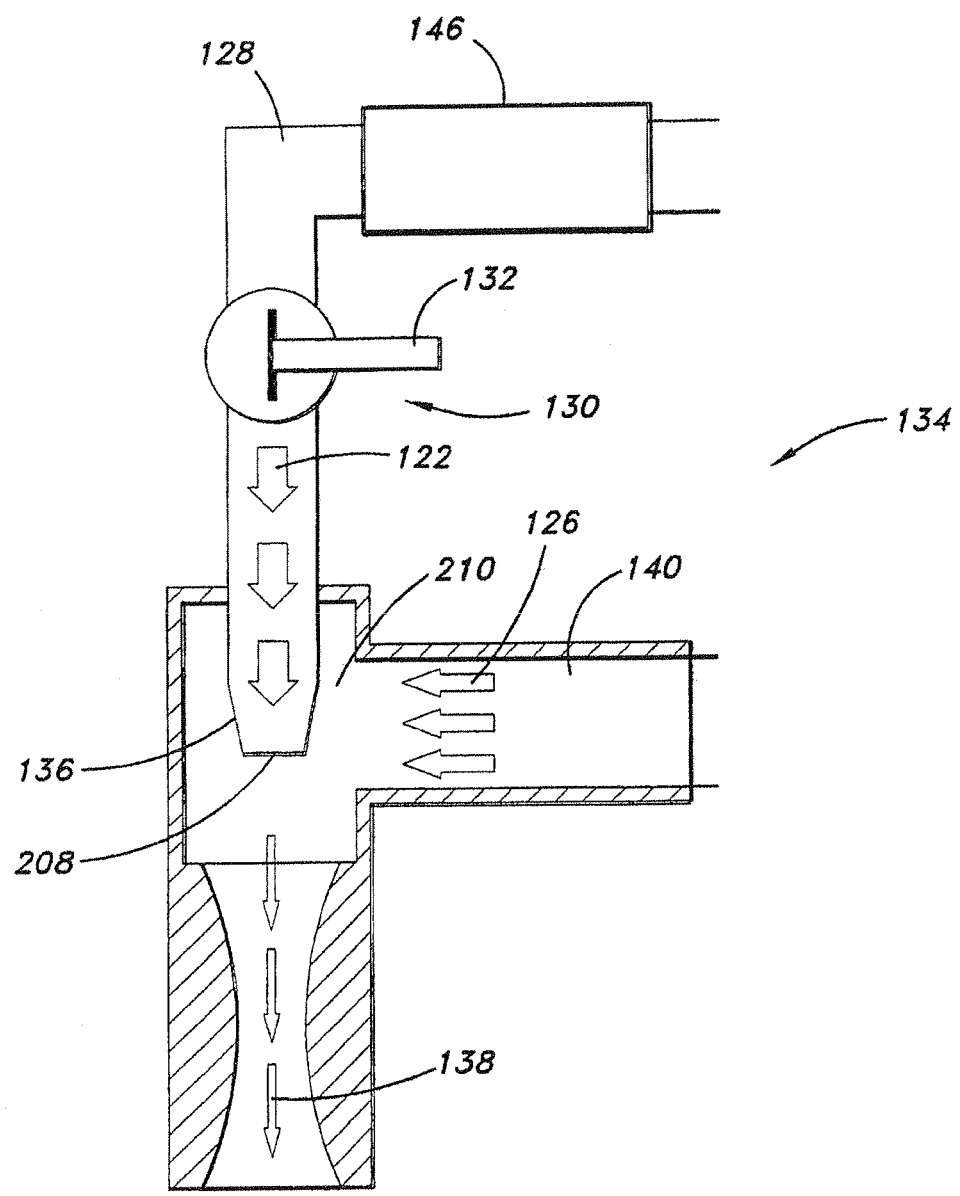
FIG. 23 illustrates the basic operation of an eductor used in the preferred embodiment of this invention.

With reference now to FIGS. 2 and 23, the operation of the eductor 134 will be illustrated. The eductor 134 includes a venturi 136. As explained above, the valve 130 is operated by the handle 132. When the valve 130 is opened, tap water from the hospital's water system flows through the venturi 136. This tap water flow is shown with reference arrows 122. It should be noted that an optional anti-backflow device 146 may be used upstream of the valve 130. Such an anti-backflow device 146 may be required by local plumbing codes as to prevent back contamination to the tap water supply. Since the operation of an anti-backflow device 146 is well known in the art, it will not be discussed further. Because of the narrower diameter at point 208, an area of lower pressure is created at point 210. This low pressure area creates a suction force at the second inlet 140 that is used to draw the waste fluid through the conduit means 32 and into the eductor 134. The waste fluid flow is shown with reference arrows 126. At this point, the waste fluids are flushed into the moving stream of tap water that is flowing at a relatively high velocity through the venturi 136 and on to the sanitary sewer 14. The combination tap water/waste fluid flow is shown with reference arrows 138.

Figure 2D:
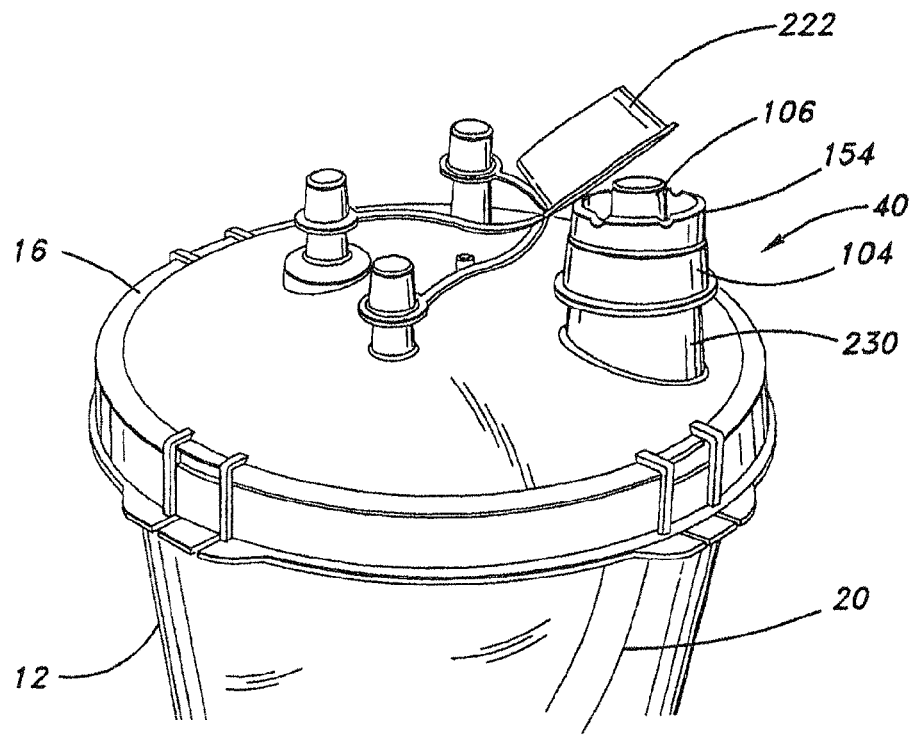
FIG. 2D is a perspective view of a first receptacle and cap similar to FIG. 2C except with a first conduit shown within the first receptacle and with a first connector shown attached to the first tower.

With reference now to FIG. 1, the conduit means 32 communicates the waste fluid from the first receptacle 12 to the pump inlet 142. Preferably the conduit means 32 includes a first conduit 20 that communicates the waste fluid from inside the first receptacle 12 to a point just above the cap 16 and a second conduit 30 that communicates the waste fluid from the first conduit 20 to the pump inlet 142. The first conduit 20 has a first end 26 and a second end 28 and a first connector 40 is attached to the second end 28 of the first conduit 20. Most preferably, as shown in FIG. 2D, the first conduit 20 extends through the first tower 230 and the first connector 40 attaches to the first tower 230 as will be discussed further below.

Figure 21:
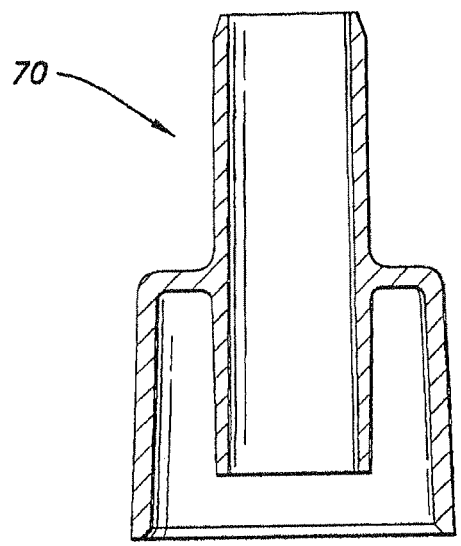
FIGS. 21-22A are of a third connector according to the invention.
Figure 22A:
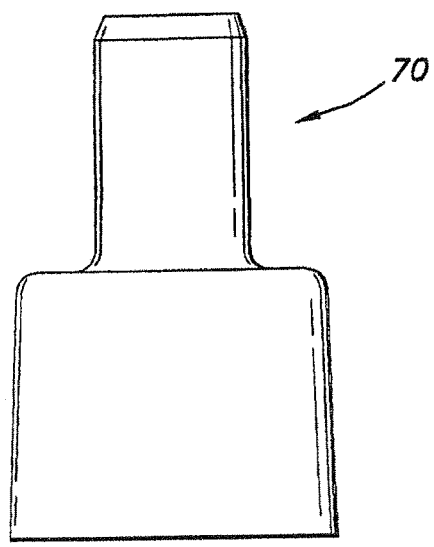
Figure 22:
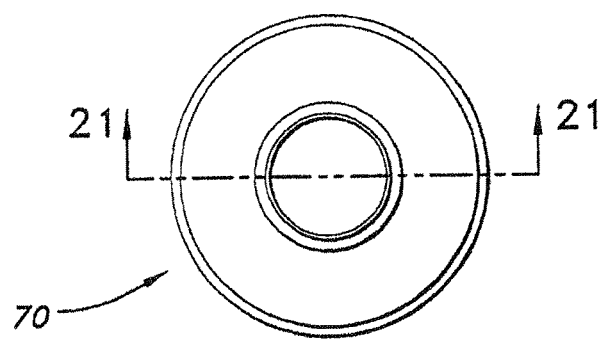

With reference again to FIG. 1, the second conduit 30 also has a first end 34 and a second end 36 with a second connector 60 attached to the first end 34. The first connector 40 easily connects to the second connector 60, defining a selectively connecting quick connect fitting, thereby connecting the first conduit 20 to the second conduit 30. A third connector 70, also shown in FIGS. 21 and 22 and 22A, is attached to the second end 36 of the second conduit 30 and easily connects to the pump inlet 142 via quick connect fitting 144.

Figure 9:
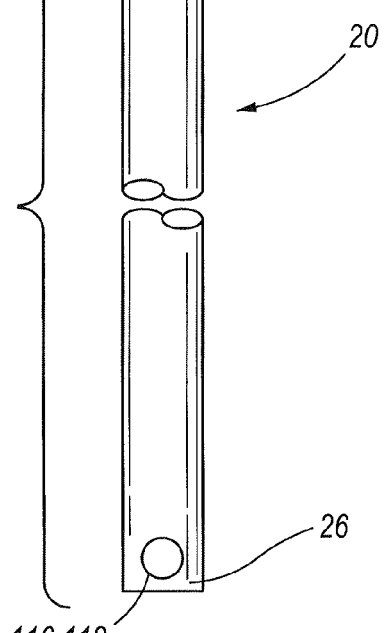
FIG. 9 is a side view of the conduit material used for the first and second conduits according to the invention.
Figure 10:
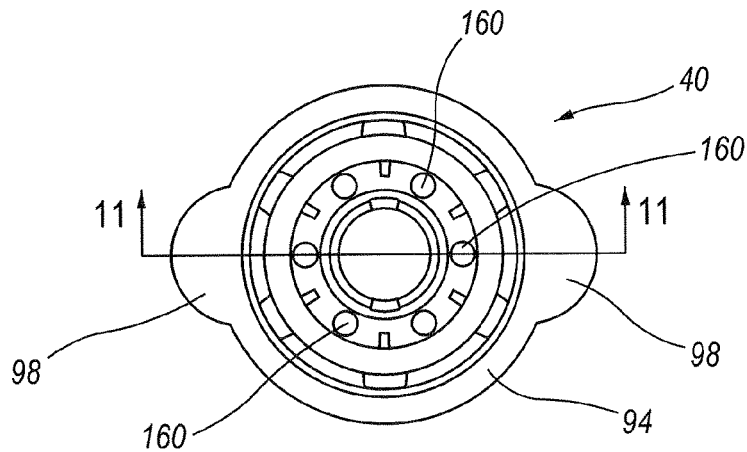
FIGS. 10-12 are further views of a first connector according to the invention.

With reference to FIG. 9, the first and second conduits 20, 30 are hollow and, in the preferred embodiment, have an interior diameter of 0.375 inches with a wall thickness of between 0.06 inches and 0.10 inches. Preferably the first and second conduits 20, 30 are flexible, bendable and resistant to kinking and resistant to collapse under vacuum pressure. It is also preferred that the first conduit 20 be of sufficient length to be usable in multiple receptacle sizes. In the preferred embodiment, at least a first hole 116, and preferably also including a second hole 118 oppositely positioned, is located near the first end 26 of the first conduit 20. The presence of holes 116, 118 reduce the likelihood of occlusion by allowing the first end 26 of the first conduit 20 to lay against the bottom of the first receptacle 12 in any alignment. The holes 116, 118 also create a total of three openings at the first end 26 of the first conduit 20 thereby maintaining fluid flow even if one of the holes becomes occluded.

Figure 2E:
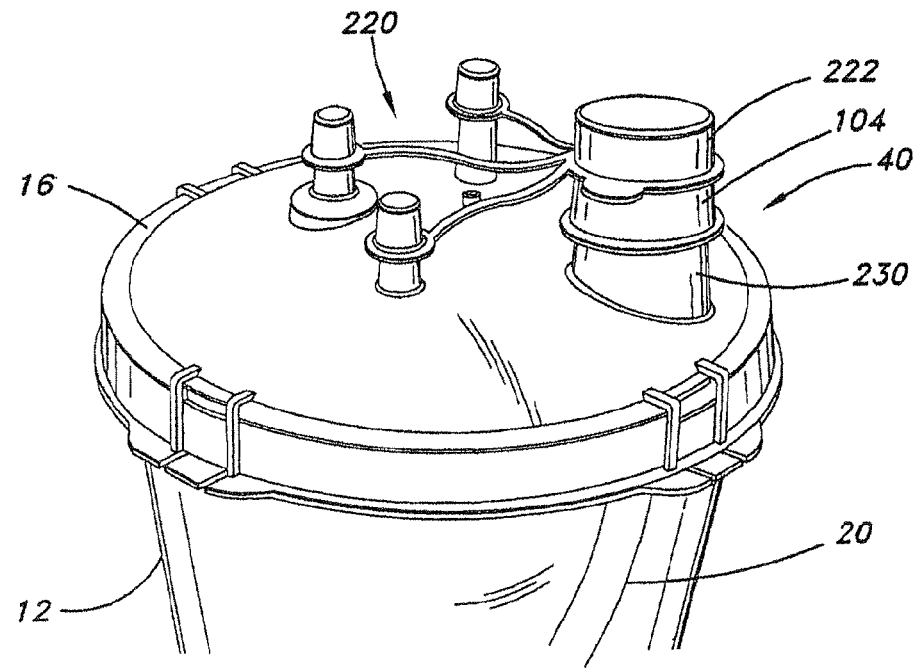
FIG. 2E is a perspective view of a first receptacle and cap similar to FIG. 2D except with the first lid shown attached to the first connector.
Figure 3:
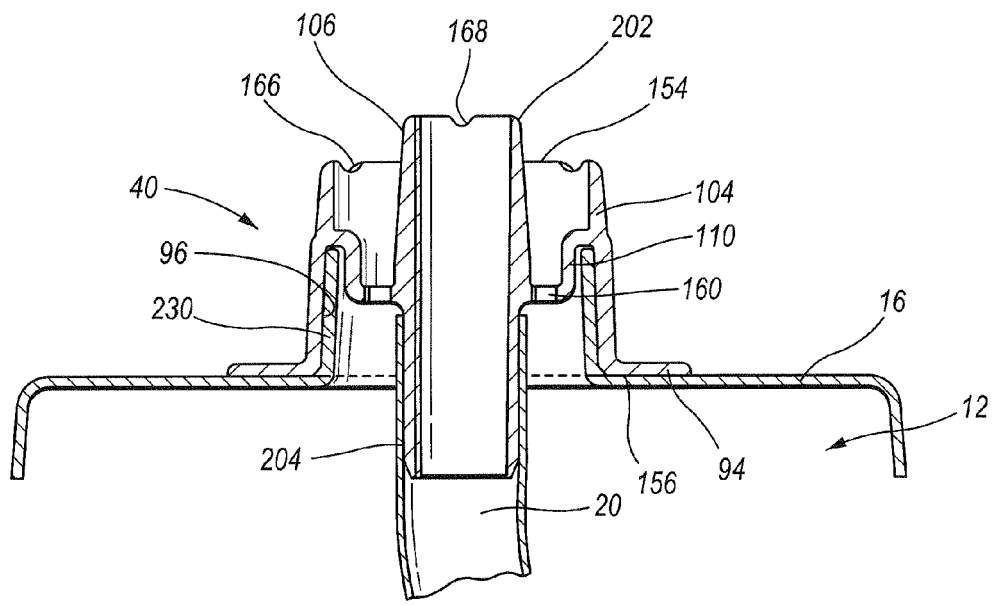
FIG. 3 is a cross-sectional view of the first connector according to the invention.

With reference now to FIGS. 1, 2, 2D, 2E, 3, and 10-12, the first connector 40 is illustrated. The first connector 40 includes an outer wall 104 and an inner wall 106. Both the outer wall 104 and the inner wall 106 have inner and outer surfaces. Preferably the inner wall 106 protrudes both above, at first end 202, and below, at second end 204, the outer wall 104, as shown. In a typical configuration, the outer wall 104 has an upper end 154 and a lower end 156. Preferably the lower end 156 includes a flange portion 94 that extends radially outward beyond the outer wall 104. Most preferably, with reference to FIG. 10, a pair of ears 98 extend radially outward beyond the flange portion 94. In the configuration shown in FIGS. 1 and 2, the lower end 156 faces inward toward the first receptacle 12 while the upper end 154 faces outward toward the second receptacle or sanitary sewer. The first connector 40 further comprises an inner support member 110 which connects the outer wall 104 to the inner wall 106. In the preferred embodiment, the inner support member 110 has the configuration as illustrated in FIG. 3, to add stability to the first connector 40. The preferred configuration also defines a groove 96, generally ring shaped, between the outer wall 104 and the support member 110.

With continuing reference to FIGS. 1, 2, 2D, 2E, 3, and 10-12, the first connector 40 may include a plurality of holes 160 and the upper end 154 of the outer wall 104 may have scallops or cutouts 166. The holes 160 can be most clearly seen in FIG. 10 while the scallops 166 can be most clearly seen in FIG. 11. The scallops 166 and holes 160 combine to enable air to flow through the space between the outer wall 104 and the inner wall 106 on either side of the inner support member 110. This enables the pressure inside the first container 12 to be equalized with pressure outside the first container 12 thereby allowing air from the atmosphere to fill the space that is left void when the waste fluid is removed from the first container 12. If manufacturing tolerances are poor, the upper end 154 may define a mating edge of the first connector 40 with the second connector 60. Even in this case, the scallops 166 provide a channel for air to flow through the space between the outer wall 104 and the inner wall 106.

Figure 11:
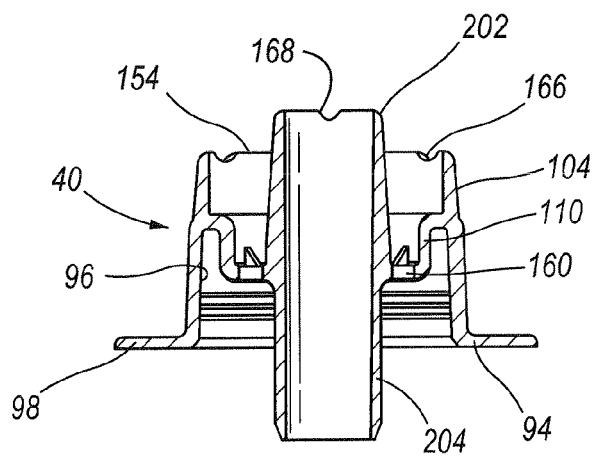
Figure 12:
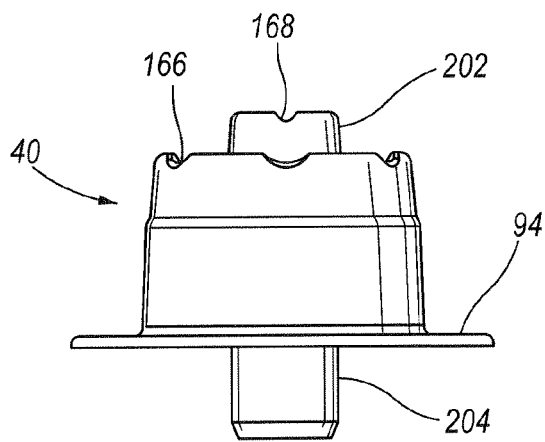
Figure 17A:
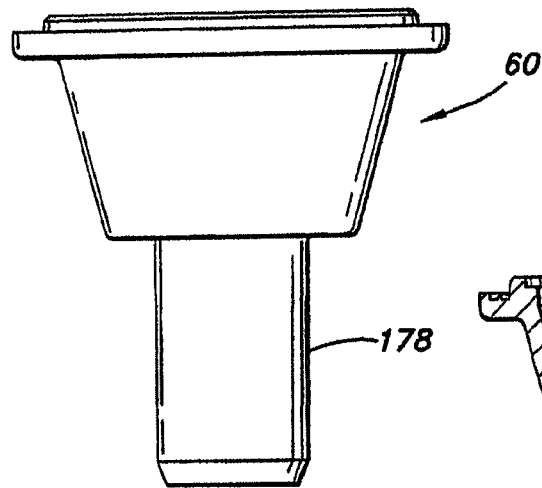
Figure 18:
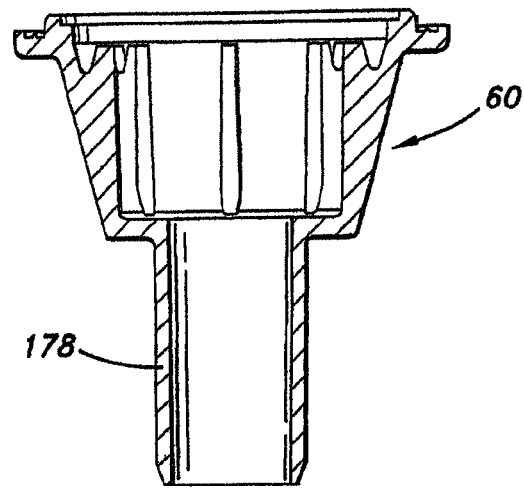
Figure 19:
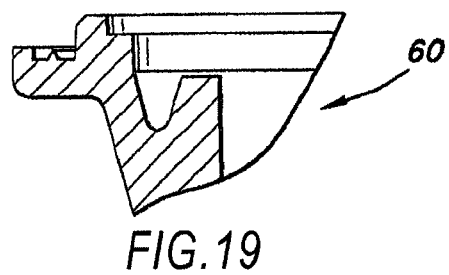
Figure 20:
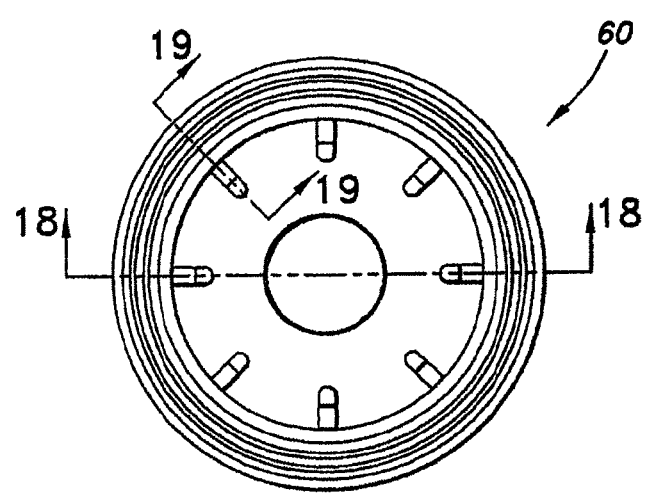

With reference now to FIGS. 2D, 3 and 11, to connect the first connector 40 to the cap 16, the first end 26 of the first conduit 20 is extended through the first tower 230 and into the first receptacle 12. The walls of the first tower 230 are then received within the groove 96 in the first connector 40. Preferably, the walls of the first tower 230 are tapered generally outward from the upper edge of the tower down to the cap 16. In this case, the first connector 40 fits easily, yet with a snug fit, as a press fit to the first tower 230. Most preferably, the first tower 230 does not contact the support member 110 but only the inner surface of the outer wall 104. If it is desired to remove the first connector 40 from the cap 16, it is only necessary to exert an upward force on the ears 98 and lift the connector 40 from the first tower 230.

Figure 4:
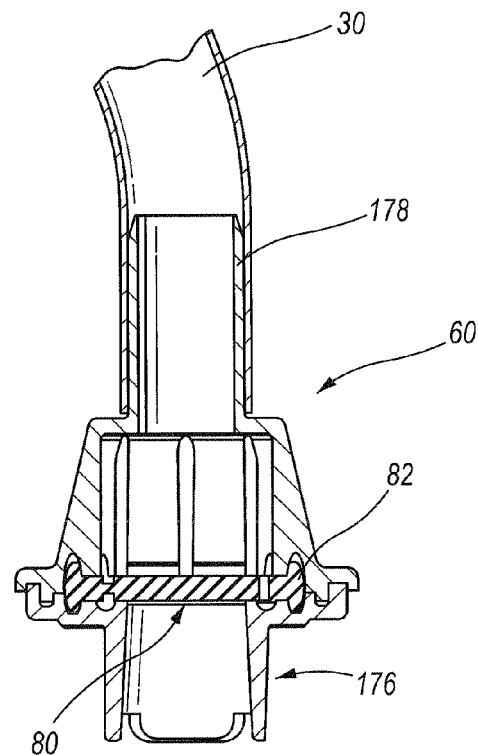
FIG. 4 is a cross-sectional view of the second connector according to the invention.
Figure 5:
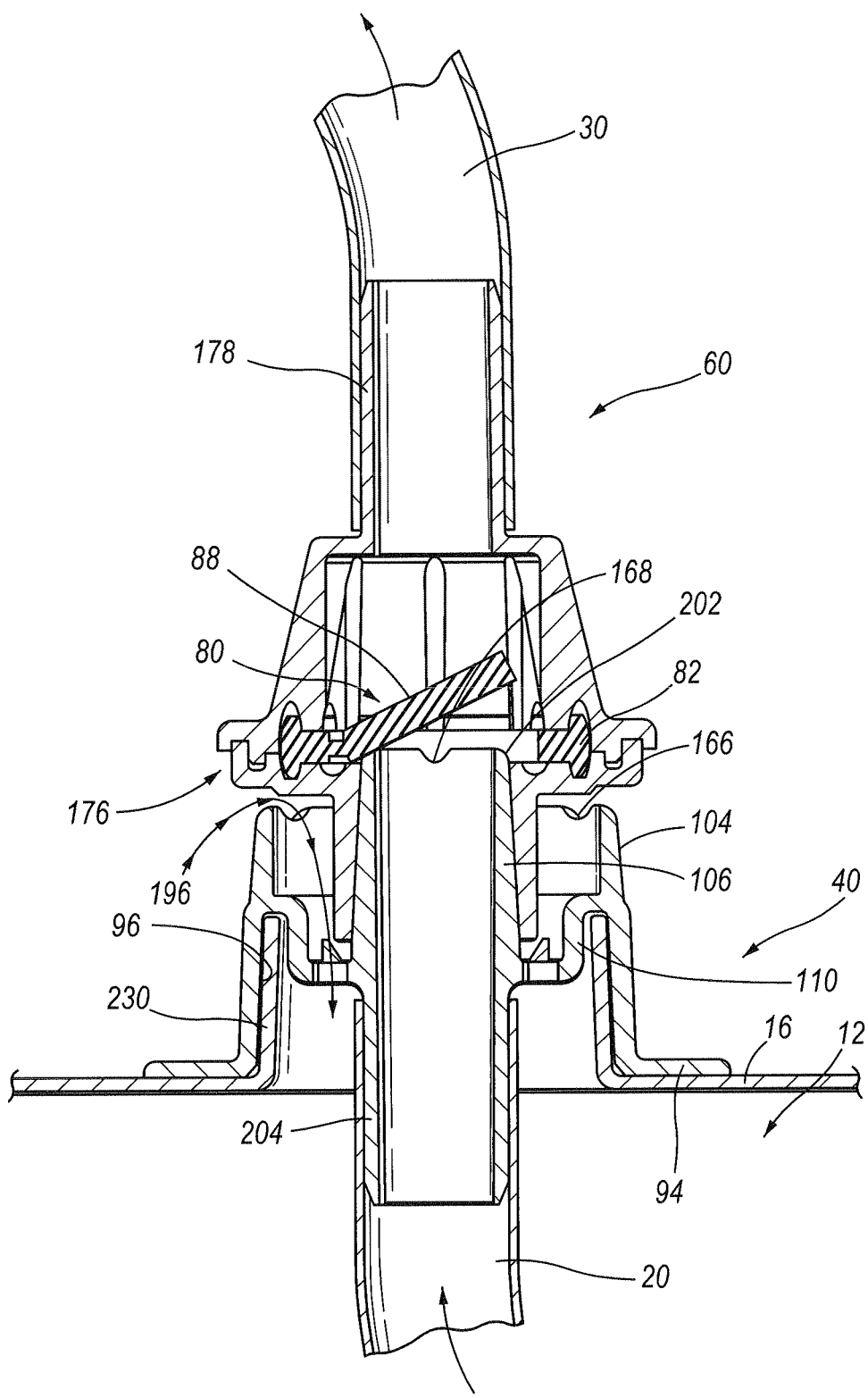
FIG. 5 is a cross-sectional view of the first and second connectors of FIGS. 3 and 4 in their connected position, and further with the flap in the open position.
Figure 6:
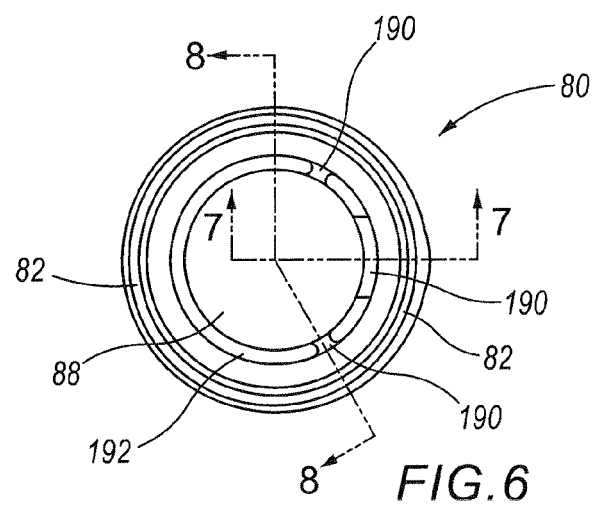
FIGS. 6, 7, and 8 are of a flow control device, including the flap.
Figure 7:
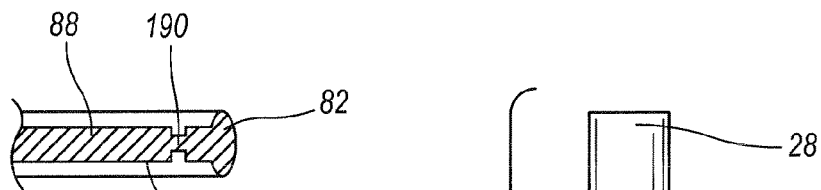
Figure 8:
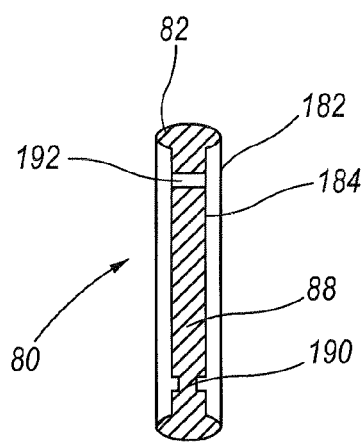

With reference now to FIGS. 4, 5, 6-8, and 13-17, the second connector 60 will now be described. The second connector 60 is comprised of three primary sections, namely the inlet 176, the outlet 178, and the flow control device 80. The inlet 176 can be most easily seen in FIGS. 13-17. As seen in FIG. 14, preferably at least a first scallop or cutout 170 is formed on the end surface of the inlet 176. More preferably three scallops 170 are evenly spaced around the end surface of the inlet 176. These scallops 170 prevent fluid backflow surge in the event that the inlet 176 is covered during use. This could occur, for example, if someone used the inlet 176 separate from the first connector 40 to "vacuum" waste fluid from a planar surface. The scallops 170 prevent the inlet 176 from forming a vacuum seal with such a planar surface. The outlet 178 can be most easily seen in FIGS. 17A-20. The flow control device 80 can be best seen in FIGS. 6-8. The flow control device 80 is made of a flexible elastomer, preferably polyisoprene. Preferably, the durometer requirement is 25-35. With continuing reference to FIGS. 6-8 and special reference to FIG. 8, the flow control device 80 comprises a disk 82 which is essentially cylindrical in shape. The outer most diameter 182 of the disk 82 is thicker than an inner most diameter 184. The inner most portion of the disk 82 comprises a flap 88. The flap 88 is hinged at one point by an elastomeric hinge 190. The flap 88 is created by the hinge 190 at one point around the circumference with a cutout 192 around the major portion of the circumference. In this way, the flap 88 can move from a first closed position to a second open position by pivoting about the hinge 190. With reference to FIG. 4, the flap is shown in the closed position while with reference to FIG. 5 the flap is shown in the open position. The second connector 60, when fully assembled, has the flow control device 80 mounted between the inlet 176 and the outlet 178. It should be noted that when the second connector 60 is not connected to the first connector 40, as shown in FIG. 4, the flap 88 acts as a check valve, allowing flow only in one direction—into the inlet 176, through the flow control device 80 and out through the outlet 178. Attempted flow in the opposite direction will fail because the flap 88 will prevent flow from passing from the outlet 178 to the inlet 176. This feature is important so that the body waste fluids do not drip or run out of the device onto the floor, onto a user, etc.

With reference to FIG. 5, the first connector 40 and the second connector 60 are shown in their operative position being connected. The first end 202 of the inner wall 106 is pressed fit against the inner surface of the inlet 176. A clear passage for air into the first receptacle 12 is shown by path 196. The flap 88 opens approximately 25 degrees to allow waste fluid flow from the first receptacle 12 through the first conduit 20 into the second conduit 30.

With reference to FIGS. 3, 5 and 11, it should be noted that preferably at least a first scallop or cutout 168, most preferably two scallops 168, is formed on the end surface of the first end 202 of the inner wall 106 of the first connector 40. As noted above, the first end 202 of the inner wall 106 contacts the flap 88. The scallops 168 help assure fluid flow from the inner wall 106 through the flap 88 by preventing the first end 202 from sticking and/or sealing to the flap 88. In this way the scallops 168 help prevent occluding of waste fluid flow at the interface of first end 202 and flap 88.

In operation, with reference to all the FIGURES, the second end 36 of the second conduit 30, being attached to the third connector 70, is connected to the suction means 22 preferably via quick connect fitting 144. The first conduit 20 is inserted into the first receptacle 12 either prior to placing waste fluid into the first receptacle or after. The first receptacle 12 is then placed within the wire basket 120. Next, the first conduit 20 is attached to the second conduit 30 by connecting the first connector 40 to the second connector 60. As explained above, this connection causes the first end 202 of the inner wall 106 to contact, and pivot the flap 88, thereby opening the flap 88 to permit fluid flow. The suction means 22 may then be activated. In the preferred embodiment, the suction means 22 is the eductor pump assembly 24 and it is activated by opening the valve 130. Once the waste fluid has been emptied from the first receptacle 12, the first conduit 20 is detached from the second conduit 30 by separating the first connector 40 from the second connector 60. Optionally, as shown in FIG. 2E, at this point the first lid 222 can be placed over the first connector 40 to close and seal the first conduit 20 and the opening 238. In order to have a well sealed connection between the first lid 222 and the first connector 40, it is preferred that the outer diameter of the upper end 154 of the outer wall 104 be similar to the outer diameter of the upper end of the first tower 230. The first conduit 20 along with the first receptacle 12 is then, preferably, discarded. The second conduit 30, including the second connector 60 and flap 88, may be reused. By discarding the first conduit 20 along with the first receptacle 12, a medical worker discarding the waste fluid is never exposed directly to the waste fluid. If another receptacle has waste fluid to be discarded, a new first conduit is inserted into the other receptacle as explained above. This new first conduit can be attached to the same second conduit 30 as explained above. Again the eductor pump assembly 24 is activated by opening the valve 130 and the waste fluid is drawn out of the other receptacle and discarded into the sanitary sewer. This new first conduit along with the other first receptacle is then preferably discarded while the second conduit 30 remains available to be reused.

The preferred embodiments have been described, hereinabove. It will be apparent to those skilled in the art that the above methods may incorporate changes and modifications without departing from the general scope of this invention. It is intended to include all such modifications and alterations in so far as they come within the scope of the appended claims or the equivalents thereof.

We claim:

1. A conduit means adapted to transport associated waste fluid from an associated receptacle, comprising:
    a conduit having a first end adapted to receive the associated waste fluid from the associated receptacle and a second end, wherein the conduit is adapted to be substantially received within the associated receptacle; and,
    a first connector attached to the second end of the conduit, the first connector having an outer wall and an inner wall that protrudes above the outer wall and is located closer to a longitudinal axis of the first connector than the outer wall, the inner wall for use in attaching the first connector to an associated second connector,
    wherein a free end of the outer wall extending away from the associated receptacle has at least one scallop formed thereon to provide a channel for air to flow through, the scallop comprising a curved indentation formed in the outer wall.

2. The conduit means of claim 1 wherein the first end of the conduit comprises a plurality of holes.

3. The conduit means of claim 1 wherein the first connector further comprises:
    an inner support member that connects the outer wall and the inner wall, the inner support member having a plurality of holes for use in enabling a pressure inside the associated receptacle to be equalized with a pressure outside the associated receptacle.

4. The conduit means of claim 3 wherein the outer wall has an inner surface that is adapted to receive at least one wall of a first tower extending from an associated cap that covers the associated receptacle.

5. The conduit means of claim 3 wherein the plurality of holes of the inner support member, in combination with the at least one scallop, combine to enable air to flow from outside the associated receptacle to inside the associated receptacle.

6. The conduit means of claim 5 wherein the outer wall of the first connector has a lower end with a flange portion that extends radially outward with respect to the longitudinal axis of the first connector and beyond the outer wall.

\* \* \* \* \*

UNITED STATES PATENT AND TRADEMARK OFFICE
CERTIFICATE OF CORRECTION

| | | |
|---|---|---|
| PATENT NO. | : 8,651,531 B2 | Page 1 of 1 |
| APPLICATION NO. | : 12/337220 | |
| DATED | : February 18, 2014 | |
| INVENTOR(S) | : Michaels et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this
Twenty-first Day of July, 2015

Michelle K. Lee
*Director of the United States Patent and Trademark Office*